United States Patent
Renz

(10) Patent No.: US 6,988,012 B2
(45) Date of Patent: Jan. 17, 2006

(54) MEDICAL-TECHNICAL SYSTEM AND OPERATING METHOD THEREFOR

(75) Inventor: Wolfgang Renz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 322 days.

(21) Appl. No.: 10/243,493

(22) Filed: Sep. 13, 2002

(65) Prior Publication Data

US 2003/0058985 A1   Mar. 27, 2003

(30) Foreign Application Priority Data

Sep. 24, 2001  (DE) ............................... 101 46 894

(51) Int. Cl.
*G05B 9/02*   (2006.01)

(52) U.S. Cl. ..................... 700/81; 424/9.3; 324/307; 324/309

(58) Field of Classification Search .................. 700/81; 324/308; 345/542; 360/77.04
See application file for complete search history.

(56) References Cited

U.S. PATENT DOCUMENTS

| | | | |
|---|---|---|---|
| 5,756,875 A * | 5/1998 | Parker et al. ................. 73/1.86 |
| 5,994,900 A | 11/1999 | Gurvich | |
| RE36,495 E | 1/2000 | Blakeley et al. | |
| 6,603,630 B1 * | 8/2003 | Gong et al. .............. 360/77.04 |
| 6,720,766 B2 * | 4/2004 | Parker et al. ............... 324/308 |
| 6,753,873 B2 * | 6/2004 | Dixon et al. ................ 345/542 |

FOREIGN PATENT DOCUMENTS

DE         195 18 621         11/1996

* cited by examiner

*Primary Examiner*—Anthony Knight
*Assistant Examiner*—Sunray Chang
(74) *Attorney, Agent, or Firm*—Schiff Hardin LLP

(57) ABSTRACT

A control device for a medical-technical system automatically acquires a status of at least one element of the medical-technical system and compares it to a reference status. When a comparison of the statuses meets a status condition, the control device implements a self-test of at least one system part of the medical-technical system. The test result is communicated to the control device and processed by it.

18 Claims, 2 Drawing Sheets

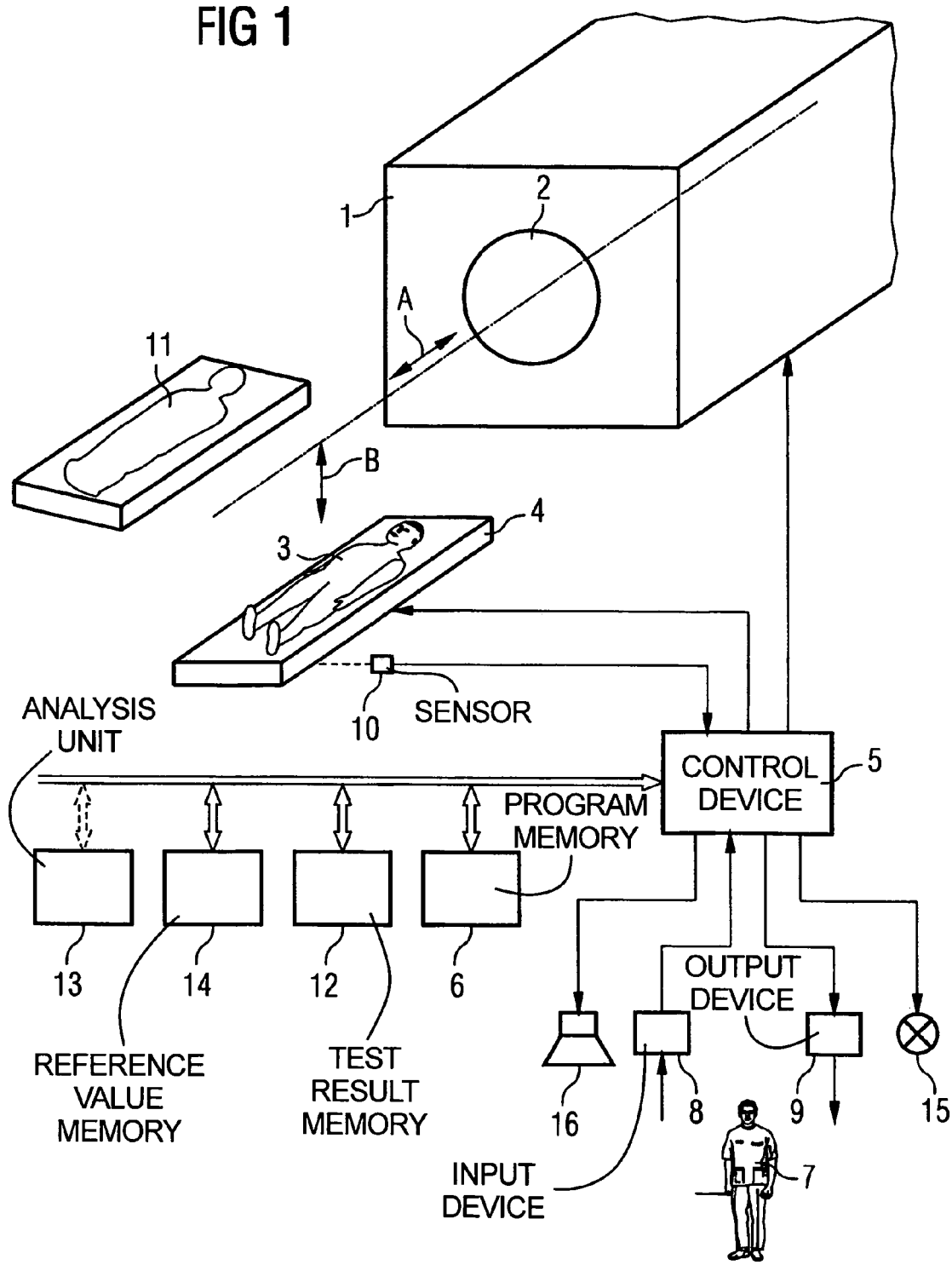

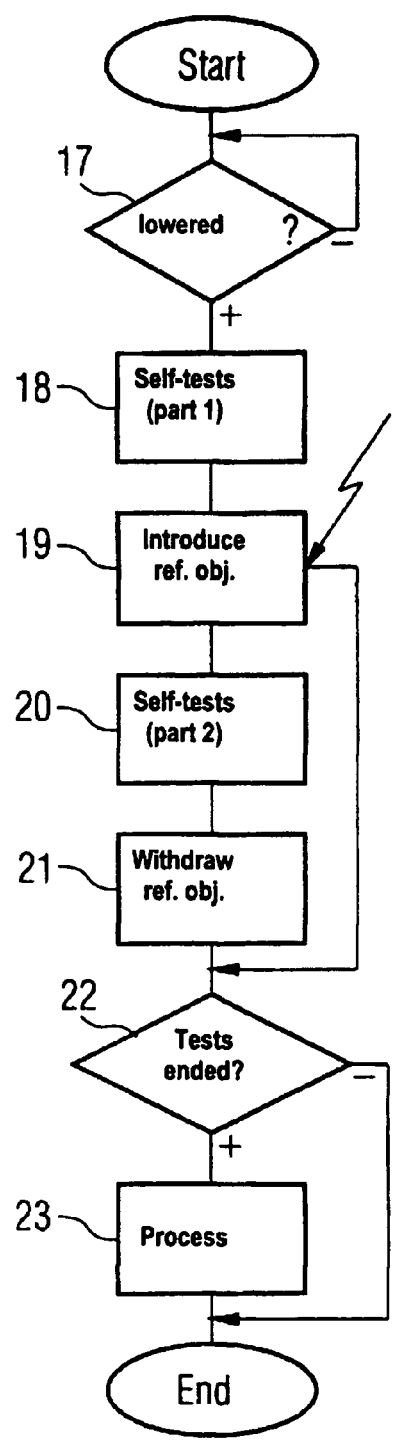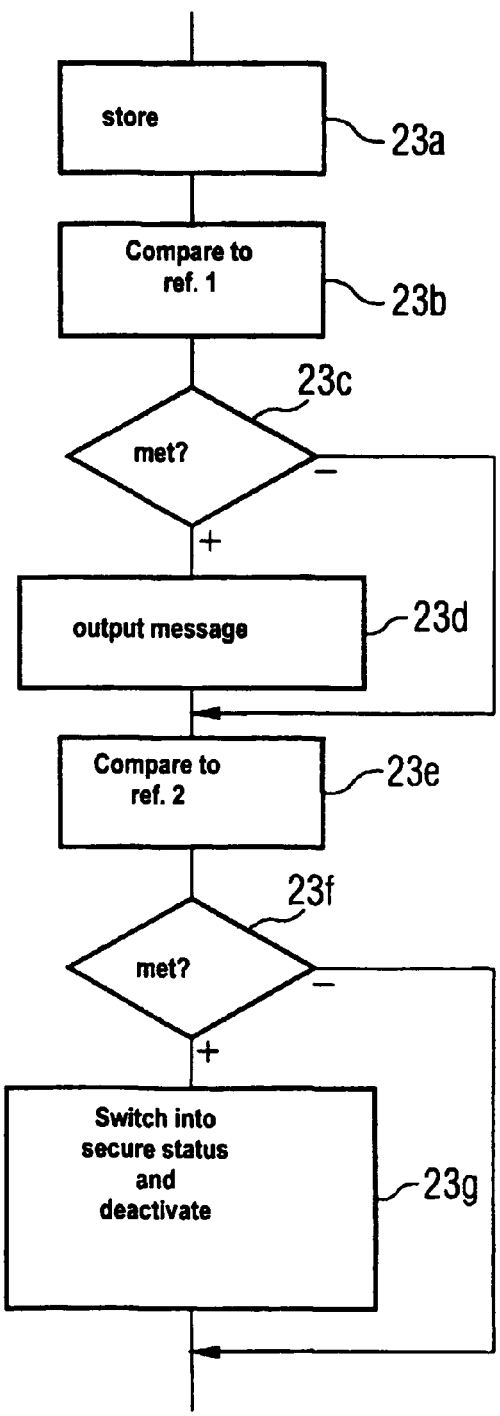

MEDICAL-TECHNICAL SYSTEM AND OPERATING METHOD THEREFOR

BACKGROUND OF THE INVENTION

1. Field of the Invention

The present invention is directed to an operating method for a medical-technical system. Examples of medical-technical systems are magnetic resonance systems, X-ray systems and ultrasound systems, particularly for tomography.

2. Description of the Prior Art

For efficient operation of a medical-technical system with optimum results, it is necessary to monitor the relevant technical system parameters of the medical-technical system at least from time to time. Only in this way, can slow and sudden changes be recognized in time and suitable countermeasures initiated.

The normal operation of the medical-technical system conventionally is interrupted for checking the system status and the relevant technical system parameters. A service technician then makes the required measurements and tests. This means an outage of use for the operator as well as a considerable time and cost expenditure.

SUMMARY OF THE INVENTION

An object of the present invention is to provide a medical-technical system and an operating method therefor which allow the medical-technical system tested in a simple, efficient way.

The object is achieved in a medical-technical system having a control device that automatically acquires the status of at least one element of the medical-technical system and compares it to a reference status, and the control device initiates a self-test of at least one system component of the medical-technical system when a comparison of the statuses satisfies a status condition, and wherein the test result is communicated to the control device and processed by the control device.

The control device need not undertake an evaluation of the test result. The processing can be limited to storing the test result so that it can be communicated later to an analysis unit connectable to the control device.

Preferably, however, the control device automatically compares the test result to a reference result and emits a message when the comparison of the results satisfies a message condition. The control device then implements an active analysis of the test result in addition to a suitable indication to a user of the medical-technical system when a proper operation is no longer possible or will not be possible for very long.

When the message emitted by the control device can be directly perceived by a human, no further technical device is required for acquiring the message. In this case, the message can be an optical and/or acoustic message.

The evaluation of the test result can even be so thorough that the control device switches the medical-technical system into a secure status as warranted when the comparison of the results satisfies a standstill condition. In this case, dangerous statuses for the system, the operator and patients can be avoided.

When, preceding the self-test, the control device triggers the introduction of a reference object into a region influenced by the operation of the medical-technical system and the self-test ensues with involvement of the reference object, an even more comprehensive self-test of the medical-technical system is possible. In particular, self-tests can be implemented that are only possible with such a reference object.

When the control device automatically triggers an immediate interruption of the self-test when the comparison of the statuses during the self-test no longer satisfies the comparison condition, then all risk to a patient can be dependably avoided, and no degradation of ongoing operation is possible. Merely the implementation of the self-test that can be delayed.

When the element of the medical-technical system is a patient acceptance device, particularly a patient bed, and the status of the element of the medical-technical system is that a position has been assumed wherein the patient acceptance device is arranged outside a region of influence of the medical-technical system, then the patient-free status of the medical-technical system can be identified in an especially dependable way.

DESCRIPTION OF THE DRAWINGS

FIG. 1 illustrates a medical-technical system in accordance with the invention in a perspective view.

FIGS. 2–3 are flowcharts which illustrate the inventive method.

DESCRIPTION OF THE PREFERRED EMBODIMENTS

As shown in FIG. 1, a medical-technical system is fashioned as an example as a magnetic resonance tomography system. The medical-technical system, however, could also be some other system, for example an ultrasound tomography system, an X-ray tomography system or some other X-ray system.

The magnetic resonance tomography system has a main area 1 with an opening 2. A patient 3 lying on a patient bed 4 can be introduced into a region of influence of the magnetic resonance tomography system via the opening 2. Medical examinations are then undertaken in this region. In the magnetic resonance tomography apparatus employed as an example, various magnetic fields are superimposed on one another in this region so that hydrogen nuclei (protons) are excited to defined magnetic resonances and the magnetic resonance signals can be received and interpreted.

The magnetic resonance tomography system—including the patient bed 4—is controlled by a control device 5 in conformity with a control program that is stored in a program memory 6. Of course, the control of the magnetic resonance tomography system ensues in interaction with control commands that are provided to the control device 5 by a user 7 via an input device 8. The measurement result of the magnetic resonance tomography system can be presented via an output device 9, for example a monitor.

As can be seen from FIG. 1, the patient bed 4 not only can be moved into the region of influence, or withdrawn therefrom, along an arrow A. The bed 4 also can be lowered or raised corresponding to an arrow B. In the lowered condition, it is thereby reliably assured that no person is located in the region of influence. The status of a lowered patient bed 4 therefore corresponds to a reference status wherein self-tests of the medical-technical system can be implemented without risk.

The position of the patient bed 4 is continuously acquired with a sensor 10 and reported to the control device 5. When the sensor signal emitted as an output by the sensor 10 indicates a lowered patient bed 4, then a status condition has been satisfied, so that the self-tests can be initiated by the control device 5. To this end, the control device 5 communicates a suitable control command to the main area 1.

Various self-tests can be implemented on the basis of the control command. For example, characteristics of the power amplifier for the transmission coils of the magnetic resonance systems can be acquired and evaluated. Further, for example, various high-frequency power checks can be compared to one another for consistency. Parameters of the radio frequency transmission coil also can be acquired. For example, the component referred to as the body tune box also can be checked for functionability (tripping the relays, detuning individual elements). Further tests are conceivable, and depend on the particular system configuration.

The test results are communicated to the control device 5 and processed by it. The control device 5 then triggers the introduction of a reference object 11 (phantom) into the influencing region. Further self-tests involving of the reference object 11 are then implemented after the introduction of the reference object 11.

For example, the power consumption of the transmission coil can be determined on the basis of the reference object 11. A check of the signal-to-noise ratio, for example, also is possible. Further, the magnetic resonance tomography system can be checked for stability. The extent of the eddy currents that are generated also can be checked. Finally, a check of components referred to as shims and of the parameters of the gradient system is possible.

These test results are communicated to the control device 5 and further-processed by it.

In the simplest case, the control device 5 merely stores the test results in a test result memory 12. In this case, they can be communicated later to an analysis unit 13 that can be connected to the control device 5.

Preferably, however, the control device 5 compares the test results to reference results. The reference results can, for example, be stored in a reference value memory 14. If a message condition is satisfied due to the comparison of the test results to the reference results, then the control device 5 can generate a message, as an output, that a person (the user 7) can directly perceive (sensory signal). For example, an optical alarm signal can be emitted via the output device 9 or a monitoring light 15. Alternatively or additionally, an acoustic message signal can be emitted via a speaker 16.

On a case-by-case basis, namely when a dangerous status of the magnetic resonance tomography system is detected, it is even possible for the control device 5 to switch the magnetic resonance tomography system into a secure status. Detecting a dangerous status thereby corresponds to comparing the test results to reference results that characterize dangerous statuses. If this comparison indicates a dangerous status exists, then the criterion for a standstill condition has been satisfied. Of course, a message is also emitted to the user 7 in this case.

The overall procedure described above ensues automatically. As warranted, however, it is possible for the implementation of the self-tests to be triggered by a control command from the user 7. In this case as well, the control device 5 acquires at least the position of the patient bed 4, and the self-test is only implemented when the patient bed 4 is in its lowered position.

According to the exemplary embodiment, further, the introduction of the reference object 11 into the influencing region also is automatically triggered by the control device 5. Here as well, it would also be possible for the user 7 to provide a suitable trigger command.

The self-tests should not negatively affect the normal operation of the medical-technical system. The control device 5 therefore initiates an immediate interruption of the self-tests if the patient bed 4 leaves its lowered position during the self-tests, i.e. the comparison condition is no longer satisfied.

The functioning of the inventive operating method is explained again below in conjunction with FIGS. 2 and 3.

As indicated in FIG. 2, a check is first made in a step 17 to determine whether the patient bed 4 has been lowered. The step 17 is repeated until the fact that the patient bed 4 has been lowered is detected, and a branch is then made to a step 18. The self-tests are implemented in the step 18, these being implementable without involvement of the reference object 11.

Subsequently, the reference object 11 is introduced into the region of influence in a step 19, for example, being moved thereinto. In a step 20, the self-tests that can only be implemented with involvement of the reference object 11 are then implemented. Finally, the reference object 11 is in turn removed, for example moved out of, the region or influence in a step 21.

After the removal of the reference object 11, a check is made in a step 22 to determine whether the self-tests have ended. When this is the case, the test results are processed in a step 23; otherwise, the test routine is exited without processing the test results.

The check to determine whether the self-tests have been ended is especially meaningful because the self-tests could be interrupted at any time if and when the patient bed 4 leaves its lowered position. This is indicated with a zig-zag arrow in FIG. 2. In this case, the self-tests are immediately interrupted and a branch is made to step 22. The reference object 11, of course, is itself removed from the region of influence if it happens to have been already introduced at this time.

As indicated in FIG. 3, the processing of the test results first includes storage in the test memory 12 according to step 23a. The stored test results are then compared to first reference results in a step 23b. A check is made in a step 23c to determine whether the comparison result satisfies a message condition. If this is the case, a message is emitted to the user 7 in a step 23d.

A step 23e then follows wherein the test results are compared to second reference results. A check is then made in a step 23f to determine whether the comparison result satisfies a standstill condition. If yes, the magnetic resonance tomography system is switched into a secure status in a step 23g and arrested therein.

In a simple way, the inventive operating method and the corresponding medical-technical system make it possible to acquire the system status for diagnostic and maintenance purposes without negatively affecting ongoing operations.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a medical-technical system having a system element and a system part, different from each other and each operated by a control device, said system element exhibiting, respectively at different times, different states of a multi-state status of said system element, said method comprising the steps of:

automatically acquiring, with said control device, a current state of said status of said system element and in said control device comparing said current state of said status to a reference status, to obtain a comparison result;

initiating, from said control device, a self-test of said system part only if said comparison result satisfies a predetermined status condition; and obtaining a test result in said system part resulting from said self-test, and communicating said test result to said control device, and processing said test result in said control device.

2. A method as claimed in claim 1 wherein the step of processing said test result comprises storing said test result in said control device and subsequently communicating said test result to an analysis unit in communication with said control device.

3. A method as claimed in claim 1 wherein the step of processing said test result comprises automatically comparing said test result in said control device to a reference result, to obtain a further comparison result, and automatically emitting a message from said control device if said further comparison results satisfies a predetermined message condition.

4. A method as claimed in claim 3 wherein the step of emitting said message comprises emitting a humanly perceptible message from said control device.

5. A method as claimed in claim 1 wherein the step of processing said test result comprises automatically comparing said test result, in said control device, to a reference result, to obtain a further comparison result, and from said control device switching at least said system part into a secure state of said status if said further comparison result satisfies a standstill condition.

6. A method as claimed in claim 1 wherein said system part has a region of influence adapted for interaction with a patient, and wherein the step of initiating said self-test of said system part includes introducing, dependent on a signal from said control device, introduction of a reference object into said region of influence, and conducting said self-test in said system part with involvement of said reference object in said region of influence.

7. A method as claimed in claim 1 comprising, in said control device, continually monitoring said status of said system element during said self-test, and automatically interrupting said self-test, from said control device, if said current state of said status of said system element fails to satisfy said reference status.

8. A method as claimed in claim 1 wherein said system part has a region of influence adapted for interaction with a patient, and wherein said system element is adapted to receive said patient to position said patient relative to said region of influence, and wherein the step of comparing said status of said system element to a reference status produces, as said comparison result, an indication of whether a portion of said patient is disposed in said region of influence.

9. A method as claimed in claim 1 wherein said system part is a magnetic resonance scanner, and wherein the step of initiating said self-test comprises initiating a self-test relating to operation of said magnetic resonance scanner.

10. A medical-technical system comprising:

a system element and a system part different from said system element, and a control device for operating each of said system part and said system element;

said system element exhibiting, respectively at different times, different states of a multi-state status of said system element;

said control device automatically acquiring a current state of a multi-state status of said system element and comparing said current state of said status to a reference status, to obtain a comparison result, and initiating a self-test of said system part only if said comparison result satisfies a predetermined status condition; and said system part obtaining a test result resulting from said self-test and communicating said test result to said control device; and said control device processing said test result in said control device.

11. An apparatus as claimed in claim 10 further comprising an analysis unit remote from said control device and in communication with said control device, and wherein said control device processes said test result by storing said test result in said control device and subsequently communicating said test result to said analysis unit.

12. An apparatus as claimed in claim 11, wherein said control device processes said test result by automatically comparing said test result to a reference result, to obtain a further comparison result, and automatically generating a message from said control device if said further comparison results satisfies a predetermined message condition.

13. An apparatus as claimed in claim 12 further comprising a message emitter which receives said message generated by said control device and wherein emits a humanly perceptible message dependent thereon.

14. An apparatus as claimed in claim 11 wherein said control device processes said test result by automatically comparing said test result to a reference result, to obtain a further comparison result, and switching at least said system part into a secure state of said status if said further comparison result satisfies a standstill condition.

15. An apparatus as claimed in claim 11 further comprising a reference object, and wherein said system part has a region of influence adapted for interaction with a patient, and wherein said control unit initiates said self-test of said system part by emitting a signal causing introduction of said reference object into said region of influence, and wherein said system part conducts said self-test with involvement of said reference object in said region of influence.

16. An apparatus as claimed in claim 11 wherein said control device, continually monitors said current state of said status of said system element during said self-test, and automatically interrupts said self-test if said current state of said status of said system element fails to satisfy said reference status.

17. An apparatus as claimed in claim 11 wherein said system part has a region of influence adapted for interaction with a patient, and wherein said system element is adapted to receive said patient to position said patient relative to said region of influence, and wherein said control device compares said current state of said status of said system element to a reference status to produce, as said comparison result, an indication of whether a portion of said patient is disposed in said region of influence.

18. An apparatus as claimed in claim 11 wherein said system part is a magnetic resonance scanner, and wherein said control device, as said self-test, initiates a self-test relating to operation of said magnetic resonance scanner.

* * * * *